United States Patent
Garcia et al.

(10) Patent No.: US 10,455,792 B2
(45) Date of Patent: Oct. 29, 2019

(54) SOYBEAN CULTIVAR TMG4177

(71) Applicant: TROPICAL MELHORAMENTO & GENETICA, Cambe/PR (BR)

(72) Inventors: Alexandre Garcia, Cambe/PR (BR); Claudio Takeda, Cambe/PR (BR); Eduardo Kawakami, Cambe/PR (BR); Romeu Afonso de Souza Kiihl, Cambe/PR (BR)

(73) Assignee: TROPICAL MELHORAMENTO & GENETICA, Cambe/PR (BR)

( * ) Notice: Subject to any disclaimer, the term of this patent is extended or adjusted under 35 U.S.C. 154(b) by 0 days.

(21) Appl. No.: 16/045,872

(22) Filed: Jul. 26, 2018

(65) Prior Publication Data
US 2019/0029212 A1    Jan. 31, 2019

Related U.S. Application Data

(60) Provisional application No. 62/537,555, filed on Jul. 27, 2017.

(51) Int. Cl.
*A01H 5/10* (2018.01)
*A01H 6/54* (2018.01)

(52) U.S. Cl.
CPC .............. *A01H 6/542* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 5,491,081 A | 2/1996 | Webb | |
| 5,977,446 A * | 11/1999 | Shannon | A01H 5/10 435/415 |
| 6,022,577 A * | 2/2000 | Chrysam | A21D 2/165 426/601 |
| 6,096,944 A | 8/2000 | Vierling et al. | |
| 6,162,967 A | 12/2000 | Webb | |
| 7,790,959 B2 * | 9/2010 | Kishore | A01H 5/10 536/23.2 |
| 2003/0005491 A1 | 1/2003 | Hauge et al. | |
| 2006/0253919 A1 | 11/2006 | Hauge et al. | |

\* cited by examiner

*Primary Examiner* — Cynthia E Collins
(74) *Attorney, Agent, or Firm* — Barnes & Thornburg LLP

(57) ABSTRACT

A soybean cultivar designated TMG4177 is disclosed. The invention relates to the seeds of soybean cultivar TMG4177, the plants of soybean cultivar TMG4177, the plant parts of soybean cultivar TMG4177, and to methods for producing progeny of soybean cultivar TMG4177. The invention also relates to methods for producing a soybean plant containing in its genetic material one or more transgenes and to the transgenic soybean plants and plant parts produced by those methods. The invention also relates to soybean cultivars or breeding cultivars, and plant parts derived from soybean cultivar TMG4177.

19 Claims, No Drawings

SOYBEAN CULTIVAR TMG4177

CROSS REFERENCE TO RELATED APPLICATIONS

This application claims priority to U.S. Provisional Patent Application No. 62/537,555 filed on Jul. 27, 2017, the disclosure of which is hereby expressly incorporated by reference in its entirety.

BACKGROUND

Soybean (*Glycine max*), is an important and valuable field crop and is the world's leading source of vegetable oil and protein meal. Thus, there is a continuing need to develop new stable, high yielding soybean cultivars that are agronomically sound. New soybeans cultivars are desired that exhibit modified phenotypical traits, including modification of growth, temperature requirements, initiation date of floral or reproductive development, increased seed yield, resistance to diseases, nematodes and insects, abiotic stress tolerance, production of better stems and roots, altered fatty acid profiles, improvements in compositional traits, and better agronomic quality. One approach to produce such new soybean cultivars is through traditional breeding techniques wherein the soybean breeder selects and develops soybean plants having traits that result in superior varieties.

There are numerous steps in the development of any novel, desirable plant germplasm. These processes, which lead to the final step of marketing and distribution, can take from six to twelve years from the time the first cross is made. Therefore, development of new cultivars is a time-consuming process that requires precise forward planning and efficient use of resources. Furthermore, due to the number of genes within each chromosome, millions of genetic combinations exist in the breeders' experimental soybean material. Thus, developing a single variety of useful commercial soybean germplasm is highly unpredictable, and requires intensive research and development. The present invention relates to a new and distinctive soybean cultivar, designated TMG4177.

SUMMARY

The present disclosure relates to a new soybean cultivar designated TMG4177 having improved resistance to soybean pests such as *Heterodera glycines*. More particularly, in one embodiment the present disclosure is directed to plants of soybean cultivar TMG4177, plant parts of soybean cultivar TMG4177 (including seeds), and methods for producing a soybean plant, wherein progeny soybean plants are produced by crossing soybean cultivar TMG4177 with itself or another soybean cultivar, and the creation of variants by mutagenesis or transformation of soybean cultivar TMG4177. In another embodiment of the present disclosure a tissue culture of cells or protoplasts is provided, wherein the cells or protoplasts are generated from a tissue of soybean cultivar TMG4177, wherein said tissue is selected from the group consisting of: leaves, pollen, embryos, meristematic cells, roots, root tips, anthers, flowers, ovule, seeds, stems, pods, and petals.

In one aspect of the present disclosure a soybean plant, or parts thereof, having all of the physiological and morphological characteristics of the soybean plant cultivar TMG4177 is provided. In one embodiment a substantially homogenous collection of seeds or a population of soybean plants is provided wherein the soybean seeds or plants have all of the physiological and morphological characteristics of the soybean cultivar TMG4177.

In accordance with one aspect of the present disclosure, a method of introducing a desired trait into soybean inbred line TMG4177 is also provided. In one embodiment the method comprises the steps of (a) crossing TMG4177 plants with plants of another soybean line that comprise a desired trait to produce F1 progeny plants; (b) selecting F1 progeny plants that have the desired trait; (c) crossing selected progeny plants with TMG4177 plants to produce backcross progeny plants; (d) selecting for backcross progeny plants that comprise the desired trait and physiological and morphological characteristics of soybean inbred line TMG4177; and (e) performing steps (c) and (d) one or more times in succession to produce the backcross progeny plants that comprise the desired trait and all of the physiological and morphological characteristics of soybean inbred line TMG4177. In one embodiment the desired trait is related to herbicide resistance, fungal resistance, insect resistance, resistance to disease, resistance to nematodes, male sterility, or enzymatic activity which alters the oil profiles, the fatty acid profiles, the amino acids profiles or other nutritional qualities of the seed.

In accordance with one aspect of the present disclosure, a method of introducing a desired trait into soybean inbred line TMG4177 is provided. In one embodiment the method comprises the steps of (a) crossing TMG4177 plants with plants of another soybean line that comprise a desired trait to produce F1 progeny plants; (b) selecting F1 progeny plants that have the desired trait; (c) crossing selected progeny plants with TMG4177 plants to produce backcross progeny plants; (d) selecting for backcross progeny plants that comprise the desired trait and resistance to the same 11 races of *Heterodera glycines* as soybean inbred line TMG4177; and (e) performing steps (c) and (d) one or more times in succession to produce backcross progeny plants that comprise the desired trait and resistance to the same 11 races of *Heterodera glycines* as soybean inbred line TMG4177.

Another aspect of this disclosure is directed to a soybean plant, seed or derived progeny which has all of the physiological and morphological characteristics of soybean inbred line TMG4177 and further contains a gene not present in soybean inbred line TMG4177 which provides herbicide resistance, fungal resistance, insect resistance, resistance to disease, resistance to nematodes, male sterility, or which alters the oil profiles, the fatty acid profiles, the amino acids profiles or other nutritional qualities of the seed. Said desired traits may be include phytase, fructosyltransferase, levansucrase, alpha-amylase, invertase, starch branching enzyme, or for example, may encode an antisense of stearyl-ACP desaturase. Said desired traits may also be directed toward herbicide tolerance, where the tolerance is conferred to an herbicide selected from the group consisting of glyphosate, glufosinate, acetolactate synthase (ALS) inhibitors, hydroxyphenylpyruvate dioxygenase (HPPD) inhibitors, protoporphyrinogen oxidase (PPO) inhibitors, phytoene desaturase (PDS) inhibitors, photosystem II (PSII) inhibitors, dicamba and 2,4-D. In one embodiment the gene is introgressed using standard breeding techniques. In an alternative embodiment the gene is introduced using recombinant transformation techniques.

The present disclosure further encompasses a method for producing a soybean seed wherein the seed is produced by the steps of crossing at least two parent soybean plants and harvesting the hybrid soybean seed, wherein at least one parent soybean plant is soybean inbred line TMG4177. The present disclosure is also directed to the resultant hybrid soybean plants grown from the hybrid seed as well as parts thereof from the hybrid seed or plant or its progeny. In particular, soybean progeny produced by crossing soybean inbred line TMG4177 with a second soybean plant are provided, wherein seed from said progeny are harvested and used to develop a derived soybean line soybean inbred line TMG4177.

In another embodiment a method for a breeding program using plant breeding techniques which employ the soybean plant TMG4177 as plant breeding material is provided, wherein the breeding material is used for performing breeding by selection techniques, backcrossing, pedigree breeding, marker enhanced selection, mutation and transformation.

DETAILED DESCRIPTION

Definitions

In describing and claiming the invention, the following terminology will be used in accordance with the definitions set forth below.

Abiotic stress: As used herein, abiotic stress relates to all non-living chemical and physical factors in the environment. Examples of abiotic stress include, but are not limited to, drought, flooding, salinity, temperature, and climate change.

Backcrossing. A process in which a breeder crosses progeny back to one of the parental genotypes one or more times. Commonly used to introduce one or more locus from one genetic background into another.

Cross-pollination. Fertilization by the union of two gametes from different plants.

Gene. As used herein, "gene" refers to a unit of inheritance corresponding to DNA or RNA that code for a type of protein or for an RNA chain that has a function in the organism.

Pedigree. Refers to the lineage or genealogical descent of a plant.

Plant Parts. As used herein, the term "plant parts" (or a soybean plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

EMBODIMENTS

As disclosed herein a new soybean inbred line, designated TMG4177, is provided including the soybean plant or any part thereof. In one embodiment a soybean plant is provided that comprises all the physiological and morphological characteristics of soybean inbred line TMG4177. In one embodiment a plant part of a soybean plant that comprises all the physiological and morphological characteristics of soybean inbred line TMG4177 is provided wherein the part is selected from the group consisting of pollen, root, seed, seed coat, cell, leaf, stem, anther, and an ovule. In one embodiment the plant part is seed.

In one embodiment a method is provided for producing soybean seed from a plant having all the physiological and morphological characteristics of soybean inbred line TMG4177. The method comprises planting seeds of soybean inbred line TMG4177, growing plants from the seed, either self-crossing/sib-crossing the plants or out-crossing the plants, and harvesting the resultant seed, wherein said seed is either an F1 hybrid or a seed of inbred line TMG4177. In a further embodiment the method comprises an additional step of treating the seed, or pre-emergent or post-emergent plant with an agrochemical agent (e.g. an herbicide) prior to the step of self-crossing/sib-crossing the plants or out-crossing the plants. As disclosed herein treating seed or plants includes direct application of the agent to the seeds or plants as well as indirect contact by applying the treatment to the soil surrounding the planted seeds or growing plants.

In one embodiment methods for introgressing a transgenic or mutant trait into soybean cultivar TMG4177 are provided. Also encompassed are soybean cultivars or breeding cultivars and plant parts derived from soybean cultivar TMG4177 that retain all the physiological and morphological characteristics of soybean inbred line TMG4177. Also encompassed by the present disclosure are methods for producing other soybean cultivars or plant parts derived from soybean cultivar TMG4177 and to the soybean plants, varieties, and their parts derived from the use of those methods. This includes soybean seeds, plants, and plant parts produced by crossing soybean cultivar TMG4177 with another soybean cultivar. Thus, any methods using the soybean cultivar TMG4177 are part of the present invention: selfing, backcrosses, hybrid production, crosses to populations, transgenic derivatives, and the like. All plants produced using soybean cultivar TMG4177, or parts thereof, as at least one parent are within the scope of this invention. Advantageously, the soybean cultivar could be used in crosses with other, different, soybean plants to produce first generation (F1) soybean hybrid seeds and plants with superior characteristics. Also included are any soybean plants obtained by transforming a plant/plant cell of soybean inbred line TMG4177 as well as the seed produced by those transgenic derivatives of soybean inbred line TMG4177.

In one embodiment a method of introducing a desired trait into soybean inbred line TMG4177 is provided wherein the method comprises: (a) crossing TMG4177 plants with plants of another soybean line that comprise a desired trait to produce F1 progeny plants; (b) selecting F1 progeny plants that have the desired trait; (c) crossing selected progeny plants with TMG4177 plants to produce backcross progeny plants; (d) selecting for backcross progeny plants that comprise the desired trait and physiological and morphological characteristics of soybean inbred line TMG4177; and (e) performing steps (c) and (d) one or more times in succession to produce the selected or higher backcross progeny plants that comprise the desired trait and all of the physiological and morphological characteristics of soybean inbred line TMG4177 listed in Table 2.

In one embodiment a method of producing hybrid soybean seed of soybean inbred line TMG4177 is provided, wherein the method comprises crossing a first inbred parent soybean plant with a second inbred parent soybean plant and harvesting resultant hybrid soybean seed, wherein the first inbred soybean plant or the second inbred soybean plant is soybean inbred line TMG4177. In one embodiment soybean inbred line TMG4177 represents the male parental line. In one embodiment soybean inbred line TMG4177 represent the female parental line. The F1 soybean seed, as well as the plants produced from such seed, are also encompassed by the present invention.

In one embodiment a plant derived from soybean inbred line TMG4177, and produced by one of the method disclosed herein, is provided, wherein the soybean plant has all of the morphological and physiological characteristics of soybean inbred line TMG4177, when grown in the same location and in the same environment, other than those characteristics altered by the presence of the relevant transgene or locus. In one embodiment the derived plant exhibits an insect, disease or herbicide resistance not exhibited by the original soybean inbred line TMG4177. In one embodiment soybean inbred line TMG4177 is modified to include a desired trait selected from the group consisting of male sterility, herbicide tolerance, insect, nematode, or pest resistance, disease resistance, fungal resistance, modified fatty acid metabolism, modified carbohydrate metabolism, drought tolerance, abiotic stress tolerance, and modified nutrient deficiency tolerances. In accordance with one embodiment the desired trait is herbicide tolerance and the tolerance is conferred to an herbicide selected from the group consisting of glyphosate, glufosinate, acetolactate synthase (ALS) inhibitors, hydroxyphenylpyruvate dioxygenase (HPPD) inhibitors, protoporphyrinogen oxidase (PPO) inhibitors, phytoene desaturase (PDS) inhibitors, photosystem II (PSII) inhibitors, dicamba and 2,4-D.

In accordance with one embodiment a method of introducing a desired trait into soybean inbred line TMG4177 is provided, wherein the method comprises: (a) crossing a plant of soybean inbred line TMG4177 with a plant of another soybean variety that comprises the desired trait to produce new progeny plants, wherein the desired trait is selected from the group consisting of male sterility, herbicide resistance, disease resistance, insect resistance, nematode resistance, modified fatty acid metabolism, modified carbohydrate metabolism, and resistance to bacterial disease, fungal disease, or viral disease, wherein a representative sample of seed of said soybean inbred line TMG4177 has been deposited under ATCC Accession Number PTA-125109; (b) selecting one or more new progeny plants that have the desired trait to produce selected progeny plants; (c) selfing the selected progeny plants or crossing the selected progeny plants with a plant of soybean inbred line TMG4177 to produce later generation selected progeny plants; (d) crossing or further selecting for later generation selected progeny plants that have the desired trait and physiological and morphological characteristics of soybean inbred line TMG4177 to produce selected next later generation progeny plants; and optionally (e) repeating the crossing or selection of later generation progeny plants of step (d) to produce progeny plants that comprise the desired trait and all of the physiological and morphological characteristics of soybean inbred line TMG4177 when grown in the same location and in the same environment. In one embodiment soybean inbred line TMG4177 is the male parent. In another embodiment soybean inbred line TMG4177 is the female parent.

One aspect of the present disclosure is directed to a commodity plant product produced from soybean inbred line TMG4177 or an F1 hybrid of soybean inbred line TMG4177, wherein a representative sample of seed of said soybean inbred line TMG4177 has been deposited under ATCC Accession Number PTA-125109 and said commodity plant product comprises protein concentrate, protein isolate, soybean hulls, meal, flour, or oil from said plant.

In accordance with one embodiment the present invention relates to a new and distinctive soybean cultivar, designated TMG4177 (experimental name: TC12-0-48.702), wherein a representative sample of seed of said soybean inbred line TMG4177 has been deposited under ATCC Accession Number PTA-125109. One advantage of this cultivar is that the cultivar is resistant (based on the female index method) to 11 races of *Heterodera glycines* (based on the scheme proposed by SCHIMITT, D. P.; SHANNON, G. Differentiating soybean responses to *Heterodera glycines* races. Crop Science, v. 32, p. 275-277, 1992).

Method Used for Obtaining the Initial Population

This line participated for two consecutive seasons in official trials in Brazil to determinate its distinctness from any other known cultivar, uniformity and stability.

TABLE 1

| Generation | Season/Year | Local | Method | Selection factor |
| --- | --- | --- | --- | --- |
| *F0 | Winter 2009 | Cambé/PR | Hybridization | — |
| F1 | Summer 2009/10 | Cambé/PR | Selfing | Disease reaction |
| *F2 | Winter 2010 | Cambé/PR | Advanced - Pedigree Method | Disease reaction |
| F3 | Summer 2010/11 | Rondonópolis/MT | Advanced - Single Plant Selection | Agronomic characteristics, incluing but not limited to, lodging, plant height and disease/nematode reactions |
| *F4 | Winter 2010 | Sorriso/MT | Seed Increase | Disease reaction |
| F5 | Summer 2011/12 | Costa Rica/MS | Preliminary Yield Trial | Agronomic characteristics, incluing but not limited to, lodging, plant height disease/nematode reaction and yield. Line TC12-0-48.702 was selected |
| F6 | Summer 2012/13 | Costa Rica/MS | Official Yield Trial | Agronomic characteristics, incluing but not limited to yield, lodging, plant height, disease/nematode reaction |
| F7 | Summer 2013/14 | Costa Rica/MS Sorriso/MR Rio Paranaiba/MT | Official Yield Trial | Agronomic characteristics, incluing but not limited to yield, lodging, plant height, disease/nematode reaction |

*Complementary irrigation.

TABLE 2

Descriptors

| Character | Code for the description |
|---|---|
| Anthocyanin pigmentation in soybean hypocotyl | Present |
| Intensity of Anthocyanin pigmentation in soybean hypocotyl | Medium |
| Flower color (R2) | Purple |
| Intensity of green color (R4) | Medium |
| Lateral leaflet shape (R4) | Pointed Ovate |
| Lateral leaflet size (R4) | Intermediate |
| Stem termination (R8) | Determinate |
| Plant Habit (R8) | Erect |
| Pubescence color (R8) | Brown |
| Pubescence density (R8) | High |
| Pod color | Dark brown |
| Relative maturity group | 4.0 a 10.0 |
| Transgenic Event | Non GMO |
| Seed size | Medium |
| Seed shape | Elongate flattened |
| Seed coat color (except hilum) | Yellow |
| Hilum color* | Yellow/Gray |
| Seed: peroxidase reaction | Negative |
| Reaction to bacterial pustule (*Xanthomonas axonopodis* pv. *glycines*) | Resistant |
| Reaction to frogeye leaf spot (*Cercospora sojina*) (races: Cs-2, Cs-4, Cs-7 e Cs-15) | Resistant |
| Reaction to frogeye leaf spot (*Cercospora sojina*) (races: Cs-23, Cs-24 e Cs-25) | Susceptible |
| Reaction to stem canker (*Phomopsis phaseoli* var. *meridionalis*/*Diaporthe phaseolorum* var. *meridionalis*) | Resistant |
| Reaction to stem necrosis (Cowpea mild mottle virus) | Resistant |
| Reaction to root knot nematodes (*Meloidogyne javanica*) | Susceptible |
| Reaction to root knot nematodes (*Meloidogyne incognita*) | Susceptible |
| Reaction to Soybean Mosaic Virus (VMCS) | Susceptible |
| Reaction to *phytophthora* root rot (*Phytophthora sojae*) race 1 | Resistant |
| Reaction to soybean cyst nematode - race 1 (*Heterodera glycines*) | Resistant |
| Reaction to soybean cyst nematode - race 2 (*Heterodera glycines*) | Resistant |
| Reaction to soybean cyst nematode - race 3 (*Heterodera glycines*) | Resistant |
| Reaction to soybean cyst nematode - race 4 (*Heterodera glycines*) | Resistant |
| Reaction to soybean cyst nematode - race 4+ (*Heterodera glycines*) | Resistant |
| Reaction to soybean cyst nematode - race 5 (*Heterodera glycines*) | Resistant |
| Reaction to soybean cyst nematode - race 6 (*Heterodera glycines*) | Resistant |
| Reaction to soybean cyst nematode - race 9 (*Heterodera glycines*) | Resistant |
| Reaction to soybean cyst nematode - race 10 (*Heterodera glycines*) | Resistant |
| Reaction to soybean cyst nematode - race 14 (*Heterodera glycines*) | Resistant |
| Reaction to soybean cyst nematode - race 14+ (*Heterodera glycines*) | Resistant |

*The color of the hilum in soybean is a genetic character controlled mainly by the interaction of 4 loci (R_, T_, I_, W_) and their allelic series. The hilum color, however, may present variations in color according to the genetic source and environmental conditions during seed production. For the soybean cultivar TMG 4177, the genetic interaction of the genes should result in gray hilum. Nevertheless, when grown in regions with elevated temperatures, usually above 35° C. during the season, the hilum color can turn to yellow. This type of variation in hilum color because of environmental conditions is well documented in the literature, even though the mechanism why it occurs is not yet fully understood.

DEPOSIT INFORMATION

A deposit of at least 2500 seeds of soybean inbred line TMG4177 has been made with the American Type Culture Collection (ATCC), 10801 University Boulevard, Manassas, Va. 20110-2209 USA, and assigned ATCC Accession Nos. PTA-125109 in accordance with the Budapest Treaty on the international recognition of deposited biological material. The seeds were deposited with the ATCC on Jun. 18, 2018. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

The present invention comprises a soybean plant characterized by molecular and physiological data obtained from the representative sample of said variety deposited with the American Type Culture Collection. Additionally, the present invention comprises a soybean plant comprising the homozygous alleles of the variety, formed by the combination of the disclosed soybean plant or plant cell with another soybean plant or cell.

The present invention provides methods and compositions relating to plants, seeds and derivatives of the soybean cultivar TMG4177. Soybean cultivar TMG4177 has superior characteristics, including resistance to *Heterodera glycines*. The TMG4177 line has been selfed a sufficient number of generations to provide a stable and uniform plant variety.

The scope of the present invention includes use of marker methods. In addition to phenotypic observations, the genotype of a plant can also be examined. There are many techniques or methods known which are available for the analysis, comparison and characterization of plant's genotype and for understanding the pedigree of the present invention and identifying plants that have the present invention as an ancestor; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

A backcross conversion, or transgenic derivative may be included as an embodiment of the present invention. Markers can be useful in their development, such that the present invention comprising backcross conversion(s), or transgene(s) are identified by having a molecular marker profile with a high percent identity such as 95%, 96%, 97%, 98%, 99%, 99.5% or 99.9% identical to the present invention.

These embodiments may be detected using measurements by either percent identity or percent similarity to the deposited material. These markers may detect progeny plants identifiable by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from an embodiment of the present soybean variety. Such progeny may be further characterized as being within a pedigree distance of 1, 2, 3, 4 or 5 or more cross-pollinations to a soybean plant other than the present invention or a plant that has the present invention as a progenitor. Molecular profiles may be identified with SNP, Single Nucleotide Polymorphism, or other tools also.

The cultivar of the invention can also be used for transformation where exogenous genes are introduced and expressed by the cultivar of the invention. Genetic variants created either through traditional breeding methods using the cultivar of the present invention or through transformation of such cultivar by any of a number of protocols known to those of skill in the art are intended to be within the scope of this invention (see e.g. Trick et al. (1997) Recent Advances in Soybean Transformation, Plant Tissue Culture and Biotechnology, 3:9-26).

Many dicots including soybeans can easily be transformed with *Agrobacterium*. Methods of introducing desired recombinant DNA molecule into plant tissue include the direct infection or co-cultivation of plant cells with *Agrobacterium tumefaciens*, Horsch et al., Science, 227:1229 (1985). Descriptions of *Agrobacterium* vector systems and methods are shown in Gruber, et al., "Vectors for Plant Transformation, in Methods in Plant Molecular Biology & Biotechnology" in Glich et al., (Eds. pp. 89-119, CRC Press, 1993). Transformed plants obtained via protoplast transformation are also intended to be within the scope of this invention. Other transformation methods such as whiskers, aerosol beam, etc. are well known in the art and are within the scope of this invention. The most common method of transformation after the use of *Agrobacterium* is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art.

Soybean is not just a seed, it is also used as a grain. The grain is used as a food source for both animals and humans Soybean is widely used as a source of protein for animal feeds for poultry, swine and cattle. The soybean grain is a commodity. The soybean commodity plant products include but are not limited to protein concentrate, protein isolate, soybean hulls, meal, flower, oil and the whole soybean itself. During processing of whole soybeans, the fibrous hull is removed and the oil is extracted. The remaining soybean meal is a combination of carbohydrates and approximately 50% protein. For human consumption soybean meal is made into soybean flour that is processed to protein concentrates used for meat extenders or specialty pet foods. Production of edible protein ingredients from soybean offers a healthy less expensive replacement for animal protein in meats as well as dairy-type products.

The invention claimed is:

1. A seed of soybean inbred line designated TMG4177, or a part thereof, wherein representative seed of the line have been deposited under ATCC Accession No. PTA-125109.

2. A soybean plant, or a part thereof, comprising all the physiological and morphological characteristics of soybean inbred line TMG4177, wherein representative seed of the line have been deposited under ATCC Accession No. PTA-125109.

3. The plant part of claim 2, wherein said part is pollen, root, seed, seed coat, cell, leaf, stem, anther, or an ovule.

4. A method for producing soybean seed, comprising: (a) planting the seed of claim 1; (b) growing plants from the seed under pollinating conditions; and, (c) harvesting seed produced by the plants grown in step (b).

5. Soybean seed produced by the method of claim 4, wherein said seed is either an F1 hybrid or a seed of inbred line TMG4177.

6. The method of claim 4, further comprising treating the seed of soybean inbred line TMG4177 with an agricultural chemical before performing step (a).

7. A soybean plant produced by growing the seed of claim 1.

8. A transgenic soybean plant comprising transformed soybean plant cells, wherein the transformed plant cells are derived from cells of the soybean plant of claim 7 and said transgenic soybean plant has all the physiological and morphological characteristics of soybean inbred line TMG4177, when grown in the same location and in the same environment, other than those characteristics altered by said transformation.

9. A seed of the soybean plant according to claim 8.

10. Pollen of the plant of claim 7.

11. An ovule of the plant of claim 7.

12. A substantially homogenous population of soybean plants of claim 7.

13. A method of introducing a desired trait into soybean inbred line TMG4177 comprising:
   (a) crossing the plants of claim 7 with plants of another soybean line that comprise a desired trait to produce F1 progeny plants;
   (b) selecting F1 progeny plants that have the desired trait;
   (c) crossing the selected F1 progeny plants with TMG4177 plants to produce backcross progeny plants;
   (d) selecting for backcross progeny plants that comprise the desired trait and all the physiological and morphological characteristics of soybean inbred line TMG4177; and
   (e) performing steps (c) and (d) one or more times in succession to produce the selected or higher backcross progeny plants that comprise the desired trait and all of the physiological and morphological characteristics of soybean inbred line TMG4177.

14. A method for producing a hybrid soybean seed comprising
   (a) crossing a first inbred parent soybean plant with a second inbred parent soybean plant; and
   (b) harvesting resultant hybrid soybean seed, wherein the first inbred soybean plant or the second inbred soybean plant is the soybean plant of claim 7.

15. An F1 soybean seed produced by the method of claim 14.

16. A soybean plant, or part thereof, produced by growing said seed of claim 15.

17. The method of claim 14, further comprising: (c) growing the progeny soybean seed from step (b) under self-pollinating or sib-pollinating conditions for about 5 to about 7 generations; and harvesting resultant seed.

18. A method of producing a soybean plant comprising a desired trait, the method comprising introducing at least one transgene or locus conferring the desired trait into a plant of claim 7, and wherein the produced soybean plant has all of the morphological and physiological characteristics of soybean inbred line TMG4177, when grown in the same location and in the same environment, other than those characteristics altered by said transgene or locus.

19. The method of claim 18, wherein the desired trait is selected from the group consisting of male sterility, herbicide tolerance, insect, nematode, or pest resistance, disease resistance, fungal resistance, modified fatty acid metabolism, modified carbohydrate metabolism, drought tolerance, abiotic stress tolerance, and modified nutrient deficiency tolerances.

\* \* \* \* \*